(12) United States Patent
Lin

(10) Patent No.: US 11,944,583 B2
(45) Date of Patent: Apr. 2, 2024

(54) ROTATABLE AND RETRACTABLE BEAUTY INSTRUMENT BASED ON SIGNAL SYNCHRONIZATION

(71) Applicant: Jinyun Lin, Zhejiang (CN)

(72) Inventor: Jinyun Lin, Zhejiang (CN)

( * ) Notice: Subject to any disclaimer, the term of this patent is extended or adjusted under 35 U.S.C. 154(b) by 448 days.

(21) Appl. No.: 17/225,092

(22) Filed: Apr. 7, 2021

(65) Prior Publication Data

US 2021/0220214 A1 Jul. 22, 2021

Related U.S. Application Data

(63) Continuation of application No. PCT/CN2020/088450, filed on Apr. 30, 2020.

(30) Foreign Application Priority Data

Dec. 10, 2019 (CN) .......................... 201911257712.0

(51) Int. Cl.
*A61H 7/00* (2006.01)
*A61N 1/32* (2006.01)
(Continued)

(52) U.S. Cl.
CPC ............. *A61H 7/005* (2013.01); *A61N 1/322* (2013.01); *A61N 5/0616* (2013.01);
(Continued)

(58) Field of Classification Search
CPC ................ A61H 7/005; A61H 2201/10; A61H 2201/1215; A61H 2201/1664;
(Continued)

(56) References Cited

U.S. PATENT DOCUMENTS 3,710,785 A * 1/1973 Hilger ................ A61H 23/0263
601/73
5,562,706 A * 10/1996 Lauterbach .......... A61N 5/0618
607/3

(Continued)

FOREIGN PATENT DOCUMENTS

CN 104918593 A 9/2015
CN 204951675 U 1/2016
(Continued)

*Primary Examiner* — Timothy A Stanis
(74) *Attorney, Agent, or Firm* — Georgi Korobanov

(57) ABSTRACT

A rotatable and retractable beauty instrument based on signal synchronization includes a main body. A back cover and a positioning head cover are respectively provided at rear and front sides of the main body. A synchronous rotating disk, a rise-fall retractable body and an active rubber body are sequentially arranged between the main body and the positioning head cover. A control main board is arranged between the main body and the back cover, and a direct-current speed-reducing motor is arranged on the control main board. A synchronous transmission circuit board is arranged on one surface of the synchronous rotating disk, and the rise-fall retractable body and multiple springs are arranged at a top of the other surface of the synchronous rotating disk. Based on the combination of the rise-fall retractable body and the synchronous rotating disk, the automatic extension and retraction is achieved.

6 Claims, 8 Drawing Sheets

(51) Int. Cl.
    *A61N 5/00*       (2006.01)
    *A61N 5/06*       (2006.01)
    *A61N 5/067*     (2006.01)

(52) U.S. Cl.
    CPC .. *A61H 2201/10* (2013.01); *A61H 2201/1215* (2013.01); *A61H 2201/1664* (2013.01); *A61H 2201/1671* (2013.01); *A61N 2005/0644* (2013.01); *A61N 5/067* (2021.08)

(58) Field of Classification Search
    CPC ............ A61H 2201/1671; A61N 1/322; A61N 5/0616; A61N 5/067; A61N 2005/0644
    See application file for complete search history.

(56) References Cited

U.S. PATENT DOCUMENTS

| | | | |
|---|---|---|---|
| 2004/0260209 A1 | 12/2004 | Ella et al. | |
| 2009/0177125 A1* | 7/2009 | Pilcher | A46B 15/0034 |
| | | | 15/4 |
| 2013/0060176 A1* | 3/2013 | Nichols | A46B 13/008 |
| | | | 601/137 |
| 2021/0001148 A1* | 1/2021 | Verheem | A61N 5/0616 |

FOREIGN PATENT DOCUMENTS

| | | |
|---|---|---|
| CN | 106236528 A | 12/2016 |
| CN | 110801379 A | 2/2020 |

\* cited by examiner

ROTATABLE AND RETRACTABLE BEAUTY INSTRUMENT BASED ON SIGNAL SYNCHRONIZATION

CROSS-REFERENCE TO RELATED APPLICATIONS

This application is a continuation of International Patent Application No. PCT/CN2020/088450, filed on Apr. 30, 2020, which claims the benefit of priority from Chinese Patent Application No. 201911257712.0, filed on Dec. 10, 2019. The content of the aforementioned applications, including any intervening amendments thereto, is incorporated herein by reference in its entirety.

TECHNICAL FIELD

This application relates to beauty equipment, and more particularly to a rotatable and retractable beauty instrument based on signal synchronization.

BACKGROUND

Beauty instrument is a common beauty apparatus in the market. The technology of the beauty apparatus have been continuously updated and improved, but there are still some shortcomings in the existing beauty instruments, for example, (1) the movable body of the head of the existing beauty instrument cannot extend and retract while rotating; (2) the working body of the head of the existing beauty instrument has a single fixed structure, so that it cannot follow the transmission light source while rotating; (3) the surface of the working body of the head of the existing beauty instrument lacks an active rubber body made based on the simulation of the human body.

SUMMARY

The object of this application is to provide a rotatable and retractable beauty instrument based on signal synchronization, which has simple structure and operation. The positioning head cover and the rise-fall retractable body rotate along with the signal synchronously, thereby realizing the integration of light, electricity, extension and retraction, and rotation. As a consequence, the beauty instrument of the disclosure is suitable for various cosmetology places.

The technical solutions of this application are described as follows.

This application provides a rotatable and retractable beauty instrument based on signal synchronization, comprising:

a main body;

wherein a rear side of the main body is clamped with a back cover, and a positioning head cover is arranged on a front side of the main body; a synchronous rotating disk, a heat sink, a rise-fall retractable body and an active rubber body are sequentially arranged between the main body and the positioning head cover; a control main board is arranged between the main body and the back cover; and a power switch, a function switch, a lithium cell, a USB charging socket, a LCD (Liquid Crystal Display) screen and a direct-current speed-reducing motor are arranged on the control main board;

a top end of the main body penetrates through the direct-current speed-reducing motor; a first blade brush contact and a second blade brush contact are arranged between the top end of the main body and the positioning head cover; a current signal source of the first blade brush contact and the second blade brush contact is connected to a control signal source of a synchronous transmission circuit board; a transmission shaft of the direct-current speed-reducing motor is provided with a first electrodeless current commutation copper tube for conducting a current signal and the synchronous rotating disk for signal synchronization; the synchronous rotating disk has a first surface and a second surface oppositely provided; the first surface is provided with a second electrodeless current commutation copper tube and the synchronous transmission circuit board; the second surface is provided with a photoelectric (laser) synchronization device and a heat sink; the first blade brush contact and the first electrodeless current commutation copper tube are connected; and the second blade brush contact and the second electrodeless current commutation copper tube are connected.

A synchronization signal is transmitted from the blade brush contacts to the synchronous transmission circuit board on the first surface of the synchronous rotating disk through the electrodeless current commutation copper tube (sheet) at the transmission shaft of the direct-current speed-reducing motor, and then transmitted to the photoelectric (laser) synchronization device on the second surface of the synchronous rotating disk to work through the synchronous transmission circuit board. The laser (2-2, as shown in FIG. 8) is irradiated on an arc surface (1-1) of the rise-fall retractable body to experience beam transformation.

In some embodiments, the heat sink is arranged on an outer side of the photoelectric synchronization device; a pin of the photoelectric synchronization device penetrates a through hole of the synchronous rotating disk, and is welded on the synchronous transmission circuit board on the first surface of the synchronous rotating disk.

In some embodiments, a plurality of positioning feet are provided on the rise-fall retractable body; the plurality of positioning feet are sleeved with the plurality of springs, respectively; the second surface is provided with a plurality of holes respectively corresponding to the plurality of positioning feet; the plurality of positioning feet are arranged in the plurality of holes, respectively; and one end of each of the plurality of springs is fixedly arranged on the corresponding positioning foot, and the other end of each of the springs is fixedly arranged in the corresponding hole.

In some embodiments, the synchronous rotating disk is made of plastic.

In some embodiments, the active rubber body has a saucer-shaped arc structure, and a radius of R angle of a surface of the active rubber body is R60-120.

In some embodiments, a radius of R angle of a top surface of the rise-fall retractable body is R60-120.

In some embodiments, one end of each of the plurality of springs is arranged at a center of the rise-fall retractable body, and the other end of each of the plurality of springs is arranged on the second surface of the synchronous rotating disk.

In some embodiments, a light guide surface is provided at a top of the rise-fall retractable body; and an inner wall of the light guide surface is provided with an arc-shaped strip to change a light beam based on working principles of a lens.

This application has the following beneficial effects.

1. This application can ensure the stable operation of the machine body when it is used for cosmetology through the limiting and positioning function, and is also conducive to cleaning and maintenance.

2. The coordination of the blade (brush) contact and the electrodeless current commutation copper tube makes the rise-fall retractable body rotates synchronously with the signal.

3. The rise-fall retractable body can automatically rise and fall according to the strength required in practical application.

4. The arc-shaped strip on the inner wall of the light guide surface at the top of the rise-fall retractable body can change a light beam based on the working principle of the lens to make the light source emit have a long emitting range, so that the light can penetrate into the deep layers of the skin to stimulate the cortex and promote blood circulation and dredging of collaterals.

5. The integrated of light, electricity, extension and retraction, and rotation is realized, enabling the rise-fall retractable body to automatically rise and fall according to the strength required in practical application can be realized.

Figure 1:
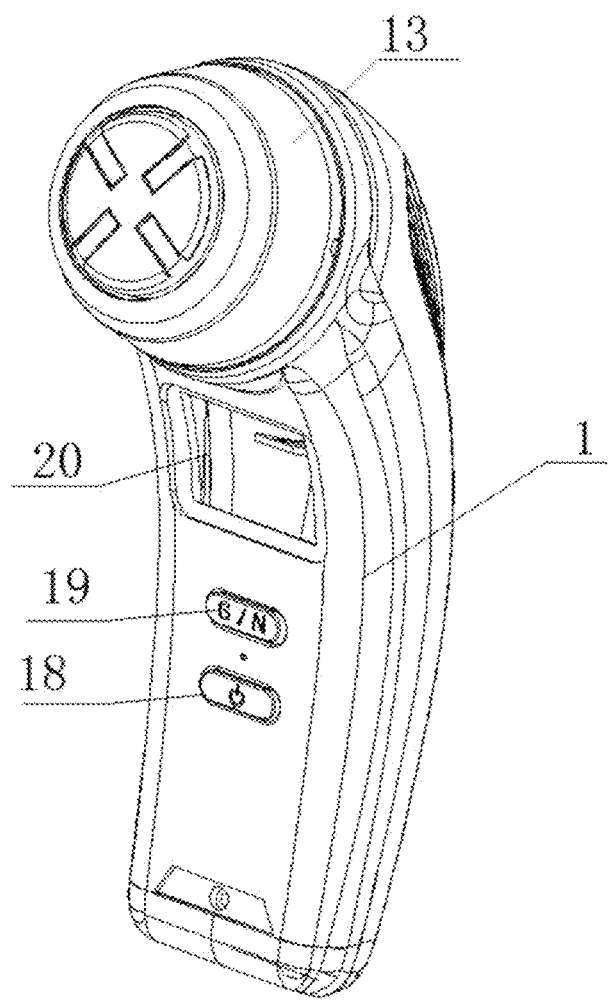
FIG. 1 is a front view of a beauty instrument according to an embodiment of the present disclosure.

In the drawings, 1, main body; 2, control main board; 3, direct-current speed-reducing motor; 4, first blade brush contact; 5, second blade brush contact; 6, synchronous transmission circuit board; 7, synchronous rotating disk; 8, photoelectric synchronization device; 9, metal heat sink; 10, rise-fall retractable body; 11, spring; 12, active rubber body; 13, positioning head cover; 14, first electrodeless current commutation copper tube; 15, second electrodeless current commutation copper tube; 16, buckle; 17, lithium cell; 18, power switch; 19, function switch; 20, LCD screen; 21, USB charging socket; 22, back cover; 23, transmission shaft; 24, positioning pin; 25, positioning pin hole; and 26, buckle positioning slot.

DETAILED DESCRIPTION OF THE EMBODIMENTS

Figure 2:
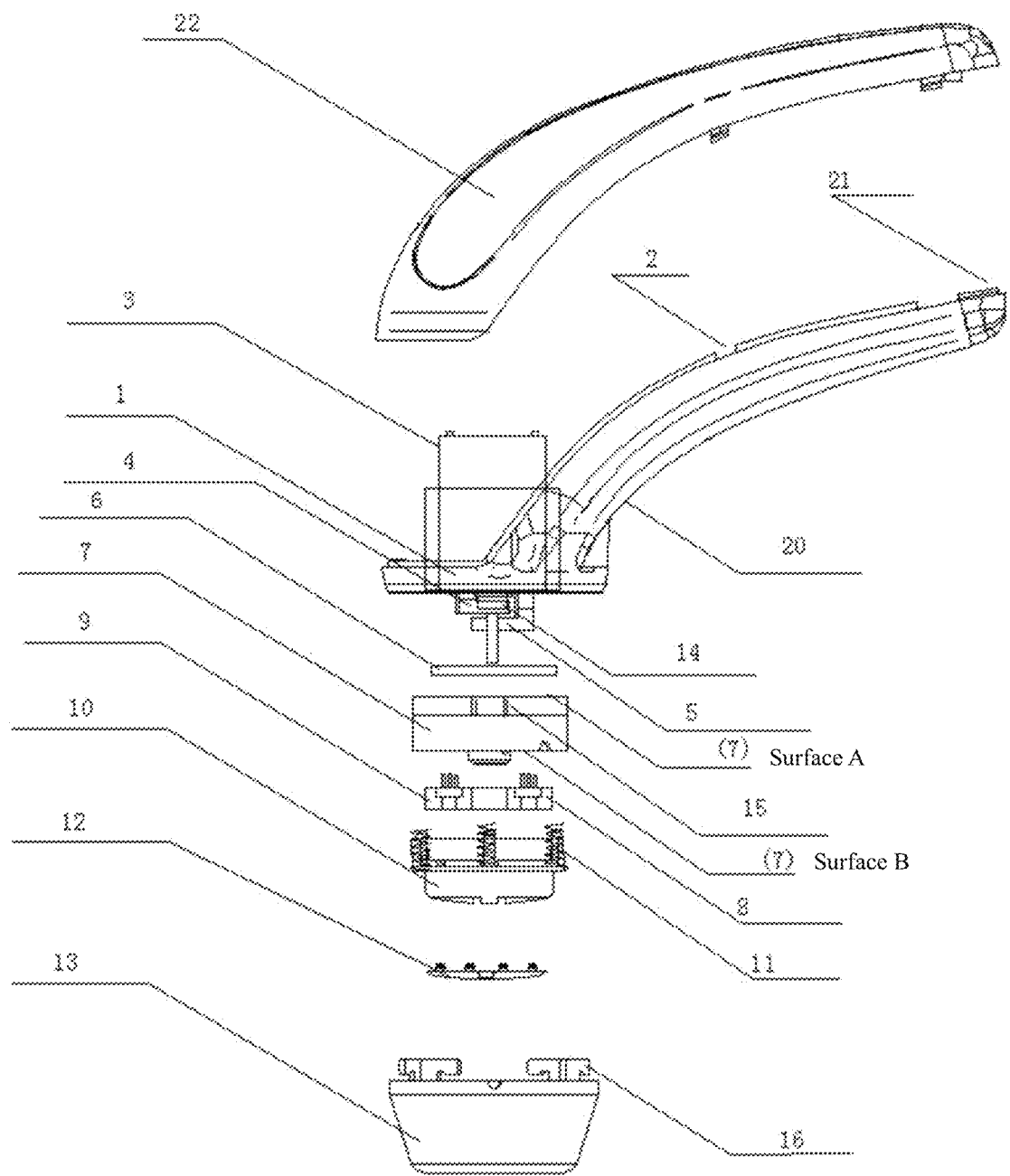
FIG. 2 is an exploded view of the beauty instrument according to an embodiment of the present disclosure.
Figure 3:
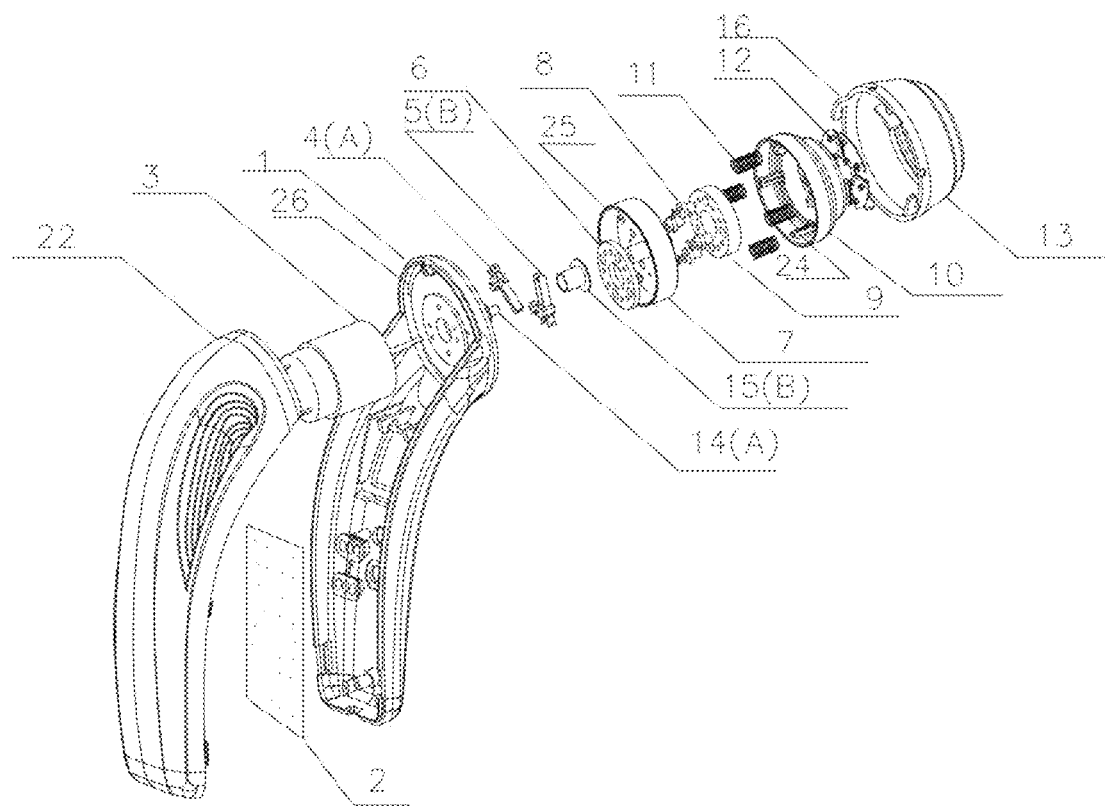
FIG. 3 is another exploded view of the beauty instrument according to an embodiment of the present disclosure in a bottom-side view.
Figure 4:
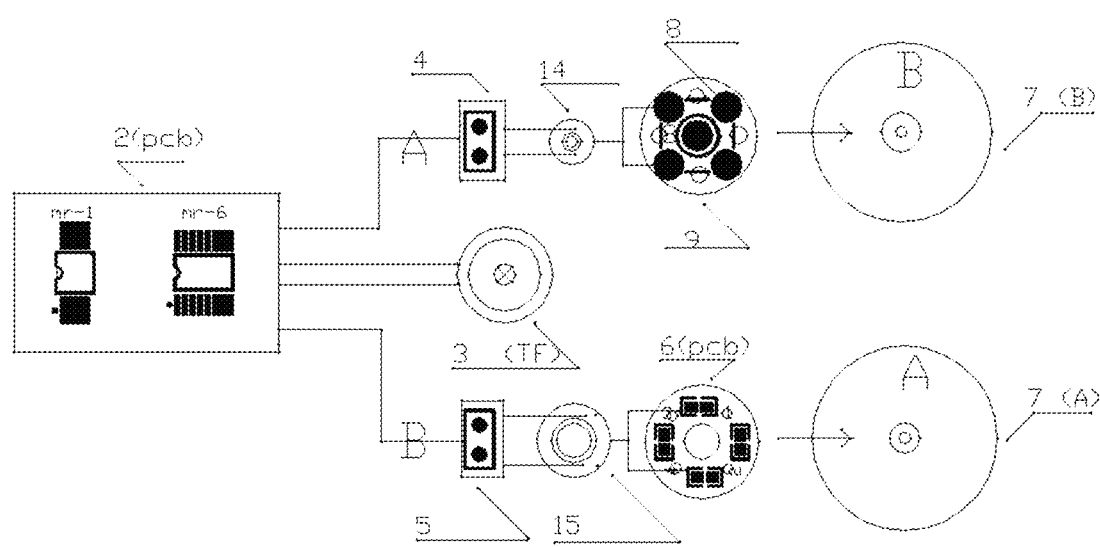
FIG. 4 schematically illustrates a transmission principle of a synchronous electrical circuit according to an embodiment of the present disclosure.
Figure 5:
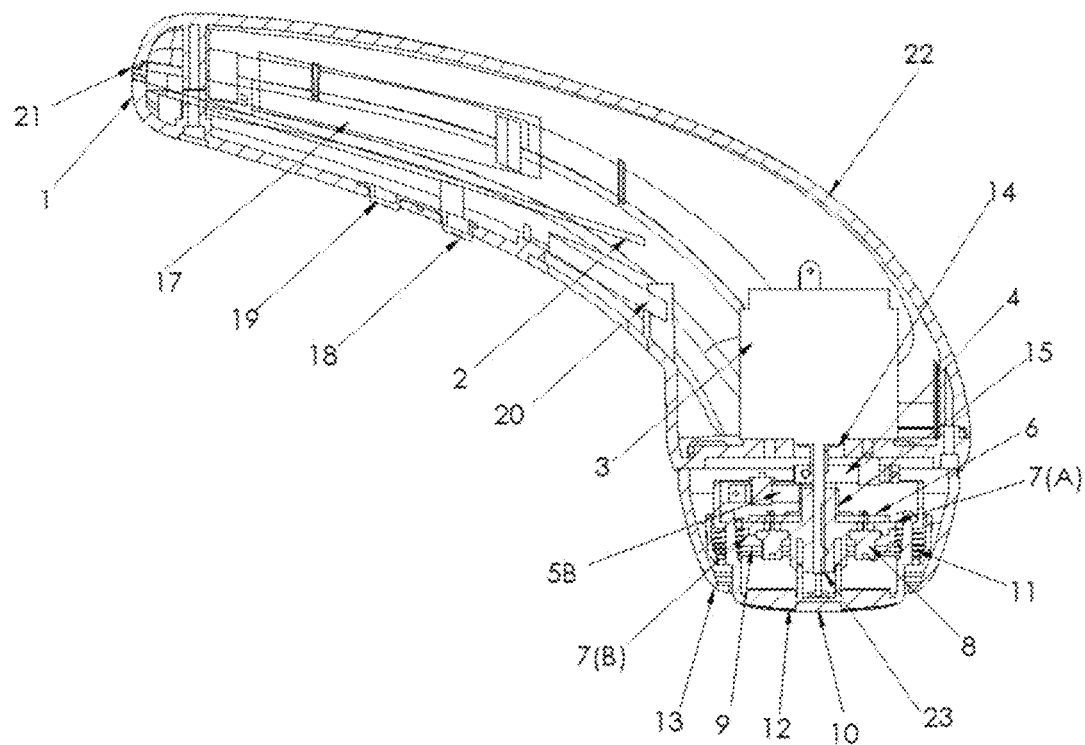
FIG. 5 is a cross-sectional view of the beauty instrument according to an embodiment of the present disclosure.
Figure 6:
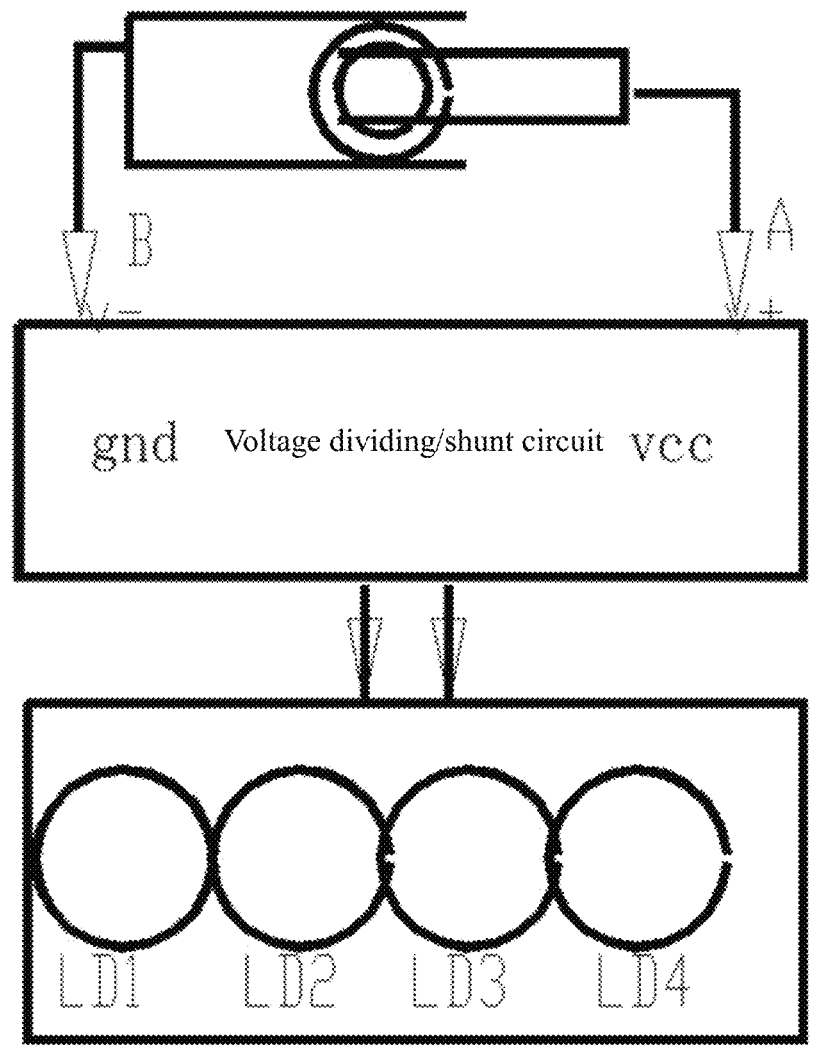
FIG. 6 is a schematic diagram of a synchronization circuit on a synchronous rotating disk according to an embodiment of the present disclosure.
Figure 7:
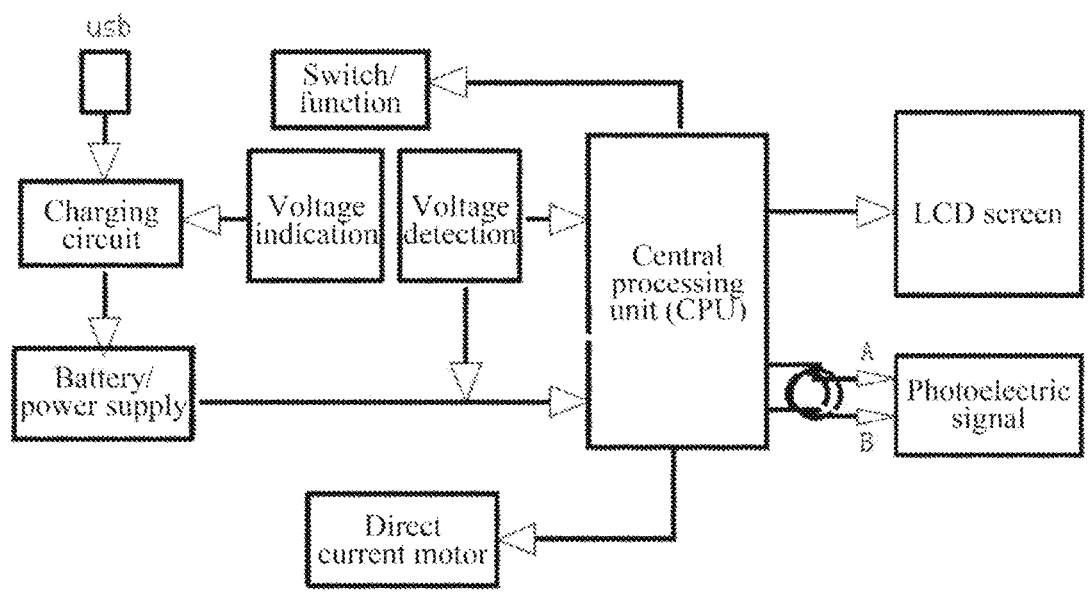
FIG. 7 is a schematic diagram of a circuit line of a main board according to an embodiment of the present disclosure.
Figure 8:
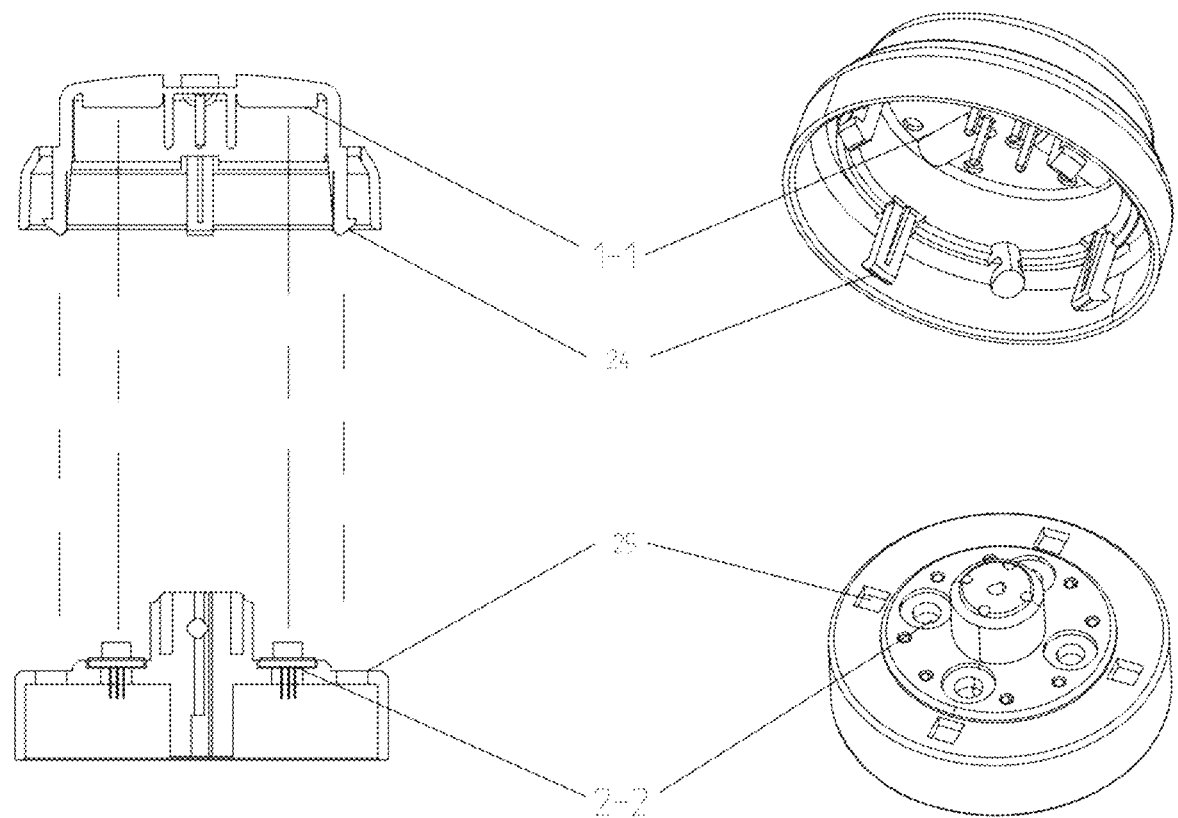
FIG. 8 schematically shows an experimental test according to an embodiment of the present disclosure.

As shown in FIGS. 1-7, this application provides a rotatable and retractable beauty instrument based on signal synchronization, which includes a main body 1. A rear side of the main body is clamped with a back cover 22, and a control main board 2 is arranged in the main body 1. A positioning head cover 13 is arranged on a head of the main body 1. A synchronous rotating disk 7, a metal heat sink 9, a rise-fall retractable body 10 and an active rubber body 12 are sequentially arranged between a base of the main body 1 and the positioning head cover 13.

The control main board 2 includes a power switch 18, a function switch 19, a lithium cell 17, a USB charging socket 21, a LCD screen 20 and a direct-current speed-reducing motor 3. The function switch 19 controls the direct-current speed-reducing motor 3 and the LCD screen 20 through the main board CPU circuit. The power switch 18, the function switch 19, and the LCD screen 20 are all arranged on the front side of the main body 1, and the USB charging socket 21 is provided at the rear of the main body 1.

The control signal source of the synchronous transmission circuit board 6 is connected to the first blade brush contact 4 and the second blade brush contact 5 arranged on the upper end of the head of the main body 1. The first blade brush contact 4 is a (VCC+) current signal source, and the second blade brush contact 5 is a (VCC−) current signal source.

The current signal source (VCC+) of the first blade brush contact 4 contacts the first electrodeless current commutation copper tube 14 at the transmission shaft 23 of the direct-current speed-reducing motor 3 through the blade of the contact. The first electrodeless current commutation copper tube 14 is closely attached to the transmission shaft 23 of the direct-current speed-reducing motor 3, and the current signal source (VCC+) is transmitted to the metal heat sink 9 on the surface B of the synchronous rotating disk 7 through the transmission shaft 23 of the direct-current speed-reducing motor 3. The screws on the metal heat sink 9 are arranged on the transmission shaft 23 of the direct-current speed-reducing motor 3, and the current signal source (VCC+) is connected to the (V+) end of photoelectric (laser) synchronization device 8 through the outer body of the metal heat sink 9. The housing of the photoelectric (laser) synchronization device 8 is V+.

The current signal source (VCC−) of the second blade brush contact 5 is transmitted to the synchronous transmission circuit board 6 connected to the surface A of the synchronous rotating disk 7 through the second electrodeless current commutation copper tube 15 arranged on the surface A of the synchronous rotating disk 7, and then transmitted to the photoelectric (laser) synchronization device 8 arranged between the surface A and the surface B of the synchronous rotating disk 7 through the synchronous transmission circuit board 6. Therefore, the current signal source (VCC+), current signal source (VCC−) and photoelectric (laser) synchronization device 8 arranged on the surface A and the surface B of the synchronous rotating disk 7 are rotate around the synchronous rotating disk 7 to work synchronously. The generated signal is transmitted and conducted through the perspective surface of the rise-fall retractable body 10. The first blade brush contact 4 and the second blade brush contact 5 are operated through the circuit signal transmission composed of the first electrodeless current commutation copper tube 14 on the transmission shaft 23 of the direct-current speed-reducing motor 3 and the second electrodeless current commutation copper tube 15 arranged on the synchronous rotating disk 7.

The rise-fall retractable body 10 is arranged on the surface B of the synchronous rotating disk 7. A plurality of positioning feet are provided at the outer end of the tail of the rise-fall retractable body 10, and the plurality of positioning feet are sleeved with the plurality of springs 11, respectively. The surface B of the synchronous rotating disk 7 is provided with a plurality of holes respectively corresponding to the plurality of positioning feet. The plurality of positioning feet is arranged in the plurality of holes, respectively. One end of each of the plurality of springs 11 is fixedly arranged on the corresponding positioning foot, and the other end of each of the plurality of springs 11 is fixedly arranged in the corresponding hole. The positioning feet on the rise-fall retractable body 10 and the spring 11 transmit the signal to the corresponding holes of the synchronous rotating disk 7. The positioning feet on the rise-fall retractable body 10 are inserted into the holes of the synchronous rotating disk 7 to form a retractable structure, enabling the whole circuit can realize the integration function of light, electricity, stretch and retraction and carry out conduction work synchronously while rotating. That is, the synchronous rotating disk 7 drives the rise-fall retractable body 10 to rotate. The rise-fall retractable body 10 is made of a transparent or non-transparent plastic, and the emission of the light source signal follows the rotation of the transparent rise-fall retractable body 10. The active rubber body 12 is arranged on the outer end of the head of the rise-fall retractable body 10.

The lifting height of the rise-fall retractable body 10 during operation is determined by the top surface of the positioning head cover 13. The positioning head cover 13 is configured to provide a limit and positioning effect to enable a stable displacement during the rotation of the rotating head. The bottom end of the positioning head cover 13 is provided with a plurality of buckles 16 which are arranged in the grooves at the bottom end of the base of the main body to facilitate installation, cleaning and maintenance.

In some embodiments, the synchronous rotating disk 7 is made of a plastic.

In some embodiments, the active rubber body 12 has a saucer-shaped arc structure, and a radius of R angle of a surface of the active rubber body 12 is R60-120.

In some embodiments, a radius of R angle of a top surface of the rise-fall retractable body 10 is R60-120.

The working principle and process of the beauty instrument provided herein are described as follows.

1. The positioning head cover 13 is configured to enable the stable operation through the limiting and positioning function, and is also conducive to cleaning and maintenance.

2. The coordination of the blade (brush) contact and the electrodeless current commutation copper tube makes the rise-fall retractable body 10 rotate synchronously with the signal.

3. The first surface of the synchronous rotating disk 7 is provided with the second electrodeless current commutation copper tube, the synchronous transmission circuit board and the photoelectric (laser) synchronous device, i.e. light-emitting tube, enabling the integration of light, electricity, extension and retraction, and rotation.

4. Through the provision of the positioning feet and the springs on the rise-fall retractable body 10 and the provision of holes on the synchronous rotating disk 7, the rise-fall retractable body 10 and the synchronous rotating disk 7 work synchronously with the light source, enabling the rise-fall retractable body 10 to automatically rise and fall according to the strength required in practical application.

5. The arc-shaped strip on the inner wall of the light guide surface at the top of the rise-fall retractable body can change a light beam based on the lens principle to make the light source have a long emitting range, so that the light can penetrate into the deep layers of the skin to stimulate the cortex and promote blood circulation and dredging of collaterals.

6. The light guide surface at the top of the rise-fall retractable body 10 is provided with active rubber body 12, which can simulate the manual massage and has high efficiency, convenient and comfortable operation performance.

Described above are only preferred embodiments of the present disclosure, and are not intended to limit the scope of the present disclosure. Any changes, modifications and improvements made by those skilled in the art without departing from the spirit of the present disclosure shall fall within the scope of the present disclosure.

What is claimed is:

1. A rotary telescopic signal synchronization beauty instrument, comprising a main body, wherein a side wall of the main body is clamped with a main body upper cover, a head of the main body is sleeved with a detachable main body positioning head cover; a rotating disk, a heat sink, a rise-fall retractable body, and a soft rubber body are arranged between the head of the main body and the detachable main body positioning head cover; an electrical mainboard control component is mounted in the main body; the electrical mainboard control component includes a power switch, a function switch, a lithium battery, a USB charging socket, an LCD screen, and a direct-current speed-reducing motor;

an inner end of the head of the main body is provided with the direct-current speed-reducing motor; an (A) path of blade brush contact and a (B) path of blade brush contact are provided at an upper end of the head of the main body and an inner end of the detachable main body positioning head cover; a motor transmission shaft of the direct-current speed-reducing motor is provided with an (A) electrodeless current commutation copper tube for current signal conduction and the rotating disk; an A surface of the rotating disk is provided with an (B) electrodeless current commutation copper tube and a transmission circuit board; a B surface of the rotating disk is provided with a photoelectric device and the heat sink, the (A) path of blade brush contact is in contact with the (A) electrodeless current commutation copper tube on the motor transmission shaft of the direct-current speed-reducing motor; the (B) path of blade brush contact is in contact with the (B) electrodeless current commutation copper tube on the A surface of the rotating disk;

a current signal source arranged on the A surface and the photoelectric device arranged on the B surface of the rotating disk are configured to rotate around the rotating disk to work synchronously, current signals from the current signal source are configured to transmit from the blade brush contacts to the transmission circuit board on the A surface of the rotating disk through the electrodeless current commutation copper tube at the motor transmission shaft of the direct-current speed-reducing motor, and then configured to transmit to the photoelectric device on the B surface of the rotating disk through the transmission circuit board to emit lights as a light source;

an upper end of the B surface of the rotating disk is provided with a rise-fall retractable body and a spring; a lifting extend-retract function is achieved between the rise-fall retractable body and the rotating disk; and an outer surface of the head of the rise-fall retractable body is provided with the soft rubber body.

2. The rotary telescopic signal synchronization beauty instrument according to claim 1, wherein the soft rubber body is in an arc-shape, and the shore hardness is 26-60 (HA).

3. The rotary telescopic signal synchronization beauty instrument according to claim 1, wherein the bottom end of the detachable main body positioning head cover is provided with a plurality of buckles, and the plurality of buckles are arranged in buckle positioning slots in the bottom end of a base of the main body.

4. The rotary telescopic signal synchronization beauty instrument according to claim 1, wherein the heat sink is arranged on the outer side of the photoelectric device; a pin of the photoelectric device is transmitted to a through hole of the rotating disk through a signal and is welded on the transmission circuit board on the A surface of the rotating disk.

5. The rotary telescopic signal synchronization beauty instrument according to claim 1, wherein an outer end of a tail of the rise-fall retractable body is provided with a plurality of positioning pins; each positioning pin is sleeved with a spring; the B surface of the rotating disk is provided with a plurality of positioning pin holes corresponding to the positioning pins; the positioning pins are arranged in the positioning pin holes; and one end of the spring is fixed on an outer wall of the positioning pin, and the other end is fixed in the positioning pin hole.

6. The rotary telescopic signal synchronization beauty instrument according to claim 1, wherein a spring is arranged in the center position of the rise-fall retractable body, and the other end of the spring is arranged on the B surface of the rotating disk.

\* \* \* \* \*